United States Patent [19]

Suzuki et al.

[11] Patent Number: 4,939,098
[45] Date of Patent: Jul. 3, 1990

[54] IMMUNOASSAY AND MEASUREMENT KIT USED THEREFOR

[75] Inventors: Masumi Suzuki; Kyoko Makiguchi, both of Katsuta; Yasushi Nomura, Mito, all of Japan

[73] Assignee: Hitachi, Ltd., Tokyo, Japan

[21] Appl. No.: 868,439

[22] Filed: May 30, 1986

[30] Foreign Application Priority Data

May 31, 1985 [JP] Japan ................................ 60-119228

[51] Int. Cl.$^5$ ......................................... G01N 33/558
[52] U.S. Cl. ..................................... 436/514; 422/50; 422/56; 422/58; 435/7; 435/300; 435/301; 435/310; 436/513; 436/515; 436/516; 436/518; 436/829
[58] Field of Search ............... 436/516, 514, 515, 829; 435/7

[56] References Cited

U.S. PATENT DOCUMENTS

| | | | |
|---|---|---|---|
| 3,482,943 | 12/1969 | Csizmas et al. | 422/58 |
| 3,930,983 | 1/1975 | Sieber | 436/516 |
| 4,018,662 | 4/1977 | Rubenstroth-Bauer | 204/299 |
| 4,198,389 | 4/1980 | Wadsworth | 435/516 |
| 4,260,392 | 4/1981 | Lee | 422/58 |
| 4,310,471 | 1/1982 | Frosch | 436/516 |
| 4,342,826 | 8/1982 | Cole | 435/7 |
| 4,717,656 | 1/1988 | Swanljung | 422/56 |

OTHER PUBLICATIONS

Chandler et al.-PCT Application WO82/02211 Published Jul. 8, 1982 Pages Cover Abstract and pp. 1-5 and 7-8.

*Primary Examiner*—Sam Rosen
*Attorney, Agent, or Firm*—Antonelli, Terry, Stout & Kraus

[57] ABSTRACT

A kit for simultaneous immunoassay of at least two items which comprises a development layer material comprising a development layer permitting development of a sample; at least two, preferably three or more, reagents supported in optional places on the development layer and individually containing an antibody or antigen different from those of the other reagents; and a concave sample-spotting place provided in the same place as one of the places where the aforesaid reagents are supported or in a place remote from all of these places. And a process for simultaneous immunoassay of at least two items which comprising utilizing said kit. The reagents supported in the above mentioned optional places are contained in microcapsules or liposomes.

10 Claims, 4 Drawing Sheets

CALIBRATION CURVE FOR α-FP

CALIBRATION CURVE FOR CRP

IMMUNOASSAY AND MEASUREMENT KIT USED THEREFOR

BACKGROUND OF THE INVENTION

1. Field of the Invention

This invention relates to an analytical process for examining at least two items, particularly an analytical process which permits analysis of a plurality of objective items of the examination in a sample by utilization of immunoreactions, and a means used for said process.

2. Description of Prior Art

As analytical processes utilizing immunoreactions, there are various known methods. For example, in Ishikawa, Kawai and Kan-i "Kosomen-eki Sokuteiho" (Enzymoimmunoassays) Igakushoin, p. 1-3 (1978), there are reviewed various methods such as radioimmunoassay, fluoroimmunoassay, enzymoimmunoassay and the like.

The radioimmunoassay requires special facilities because it uses radioactive substances, and hence it is disadvantageous in general utility. Further, in the case of immunoassays according to the radioimmunoassay and the enzymoimmunoassay, it is difficult to analyze a plurality of components in a slight amount of the same test sample at the same time because of the limitation derived from the principles of the immunoassays. Therefore, in conducting immunoassay of various components or items in a test sample, the test sample should be diluted and divided for testing each component and the reaction of a specific component in a test sample with a corresponding reagent should be carried out. Thus, conventional immunoassays have been disadvantageous in that large amounts of samples and reagents are needed for analyzing a plurality of objective components.

Further, there has not yet been reported a simple and convenient analytical means for analyzing at least two of such components at the same time.

SUMMARY OF THE INVENTION

An object of this invention is to provide an analytical process by which reactions of at least two objective items are caused for a specific sample obtained by one sampling, and qualitative or quantitative analysis of these items can be conducted; and a means used for said process.

This invention utilizes the fact that an immuno-reaction is specifically effected between a specific component and a specific reagent.

One aspect of this invention relates to an analytical process which comprises supporting at least two reagents each comprising an antigen or antibody different from those of the other reagents in different places on a development layer material permitting development of a sample, placing a sample in a specific place on the aforesaid development layer material, moving the sample therein, and observing reaction products after the sample passes the above-mentioned reagent-supporting places.

Another aspect of this invention relates to a means, i.e., kit used for the above-mentioned analysis.

According to this invention, there is provided a process which is simple, makes it possible to analyze a plurality of items (components and the like) in a sample such as blood, urine or the like at the same time by utilizing immunoreactions, and is very advantageous for analyzing a large number of samples at a time for a plurality of testing items in each sample.

In the said figures, the following signs and figures which denote the meanings shown below are used:

a . . . anti-IgG, b . . . anti-IgA, c . . . anti-IgM, $a_1$ and $a_2$ . . . microcapsules, d, e and f . . . spotting places, g . . . a sample-spotting place, h . . . a development layer, i . . . a mesh, 10 . . . a development layer material, 11 . . . a buffer for electrodes, 12 . . . gel, 12a . . . a separating-gel containing liposome having anti-CRP bound thereto, 12b . . . a separating-gel containing liposome having anti-α-FP bound thereto, 12b . . . a concentrating gel, B and C . . . electrodes.

DESCRIPTION OF PREFERRED EMBODIMENTS

The means, i.e., kit used in this invention comprises a development layer material comprising a development layer permitting development of a sample; at least two, preferably three or more, reagents supported in optional places on the development layer and individually containing an antibody or antigen different from those of the other reagents; and a sample-spotting place of preferably concave form provided on the development layer material in the same place as one of the places where the aforesaid reagents are supported or in a place remote from all of those places.

As the development layer, a layer made of any material may be used so long as it permits holding or immobilization of the reagents by physical adsorption or chemical bond, and movement of the sample by a means such as electrophoresis, a solvent or the like. In general, there are exemplified gels of organic substances such as synthetic polymers, polysaccharides, proteins and the like; gels of metal hydroxides; clay minerals such as zeolites, montmorillonites and the like; and porous glass beads, porous plastic film and the like which in some cases have on the surface a polar group such as amido group given by surface treatment with ion-exchange resin.

The synthetic polymers include those having polar groups such as polyacrylamide, polyurethane, polyvinyl alcohol, polyvinylpyrolidone and the like. The polysaccharides includes agarose, and the like. The proteins include collagen, gelatin, and the like. The metal hydroxides include aluminum hydroxide, titanium hydroxide, and the like.

In forming the development layer material, a flat plate made of glass or the like may be used as an auxiliary material.

Figure 2:
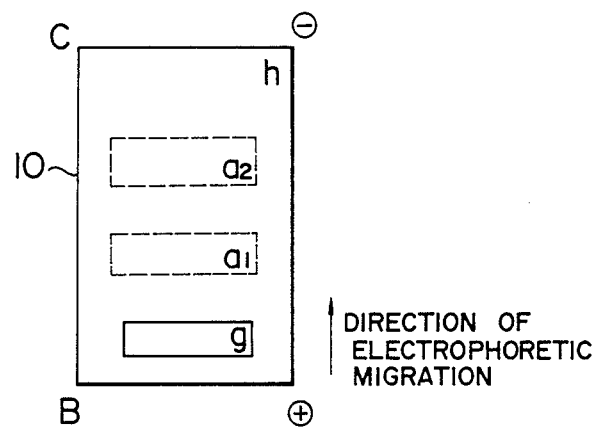
FIG. 2 is a scheme of a development layer material which is another embodiment of the means of this invention.

The development layer material can be formed by a conventional method. For example, when agarose gel is used, a glass plate (width×length×thickness=4 cm×7 cm×2 mm) having as shown in FIG. 2 a plurality of concave portions for fixing reagents is prepared, and a solution of liposome is placed in the concave portions (wells). To the liposome has previously been bound an antibody or antigen which reacts with an objective substance as an object of measurement. Next, a mesh (made of a porous substance: pore size 0.2 μm) is placed on the solution, followed by placing thereon agarose gel (2%) prepared by dissolution in phosphate buffer (pH 7.4). The portion other than the wells containing the liposome and that for sample-spotting place, namely, the glass surface not adsorbing the gel is warmed to adsorb the agarose gel to a thickness of 1 to 1.5 mm.

Although the shape of the development layer is usually reactangular, it may be circular or square.

The size of the development layer depends on the kind of sample, the kind of substances to be measured and the like, or on a measuring apparatus in the case of measurement by an optical means. Selection of the size is within the technical scope of those skilled in the art. The size is usually width×length=4 cm×12 cm.

Although the thickness of the development layer is also properly selected depending on purpose of use, it is usually 2 mm in the case of using cellulose gel such as Sepharose (trade mark: distributed by Pharmacia) or the like and 1 to 1.5 mm in the case of using agarose or the like (in both cases, the term "the thickness of the development layer" used here means the thickness of the gel or development layer itself and does not include the thickness of a support such as glass).

It is sufficient that the sample-spotting place on the development layer is formed so as to have a hollow of suitable size. Usually, the hollow has a rectangular, circular, square or the like form, and its sufficient depth is 1 mm or less.

As a method for supporting the reagents on the development layer, a means such as physical adsorption or chemical bonds are used. The chemical bonds can be attained by using substances having an ability to bind to an antibody or antigen to an antigen or antibody which is an objective substance of examination.

The reagents may be used either by binding them directly to a material for forming the development layer, or by enclosing them in microcapsules and then fixing the microcapsules on the development layer by utilizing physical adsorption or chemical bonds. In this case, a porous material may be interposed between the microcapsules and the development layer. As the porous material, porous glass beads and the like are used. As the microcapsule, any one may be used so long as its surface undergoes lysis by antigen-antibody reaction or complement activity, and crythrocyte of an animal, e.g., sheep, and liposome can be used. Erythrocytes of animals other than sheep and animal cells other than etythrocyte can also be used as the microcapsule in this invention when the antibodies or antigens can be bound to the cell membrane.

In the case of erythrocyte or animal cell, the dialysis method [Mitsuru Furusawa "Seikagaku" (Biochemistry) 53 (9), 1066(81')] or the like is applied. By this method, cell sap and the like are discharged from the erythrocyte or animal cell, and for example, enzymes can be placed therein.

In the case of liposome, it is used as a capsule membrane by binding to the antibody (or antigen) by a conventional method [Lee et al., Nature, 288, 602 (1985)], followed by formation of a liposome membrane (by a method described, for example, in S. W. Chan et al., Methods in Enzymology 74, 152–161).

The antibody (or antigen) is enclosed in the membrane by a conventional method.

As to substances to be enclosed in the microcapsule, in addition to the antibody or antigen which reacts with an objective substance of detection, there may be incorporated together therewith a detectable label substance which reacts with the objective substance. As the label substance, chelating agents, enzymes, coenzymes and fluorescent substances are used.

The chelating agents include 2-(2-thiazolylazo)-4-methyl-5-sulfomethylaminobenzoic acid (hereinafter referred to as TAMSMB) which reacts specifically with copper ion and cobalt ion; Na salt of 2-(5-bromo-2-pyridylazo)-5-(N-propyl-N-sulfopropylamino)phenol (abbreviated sometime as 5-Br-PAPS) which reacts with Zn ion; and 2-nitroso-5-(N-propyl-N-sulfopropylamino)phenol (abbreviated sometimes as Nitroso-PSAP) and Na salt of 2-(5-bromo-2-pyridylazo)-5-(N-propyl-N-sulfopropylamino)aniline which react with iron ion.

As the enzymes, there may be used enzymes having enzymatic activity by themselves and apoenzymes having enzymatic activity in the presence of coenzymes.

It is also possible to develop a detectable label substance afterward which does not react with the substances supported on the development layer but reacts with reaction products newly produced by the reactions of the supported substances with objective substances of examination.

Formation of a sample-spotting place in the form of a well on the development layer is convenient for spotting a sample to develop the same in the development layer.

In supporting the reagents, the distance between the reagents is not critical, that is, any place on the developing layer can be chosen. It is sufficient that the distance between them is such as contaminants are shut out of the detection systems.

The antibodies or antigens to be supported on the development layer can optionally be selected depending on the kind of objective substances of examination.

The examination process which is another aspect of this invention is practised by using a means for examination constructed in the manner described above. In detail, this aspect of the invention relates to a process for qualitatively or quantitatively analyzing two or more objective components in the same sample at the same time by using an optical or electric means, which comprises spotting a sample in the sample-spotting place of the means for examination, moving the sample in the development layer toward reagents supported on the development layer, subjecting each reagent supported on the development layer to immunoreaction specifically with each objective component in the sample (cognate antigen or cognate antibody in said sample) at a destination corresponding to the component in the sample, and observing substances which have undergone a physical change (color change or outflow from capsules) concomitantly with the immunoreaction. In this case, favorable results can be obtained when there is used a means having microcapsules which have an antigen or antibody reactive specifically to an objective component in the sample and bound to their surfaces, and contain a detectable substance inside them. The reagents supported on the development layer need not necessarily contain a detectable substance, and it is sufficient that they contain only substances which react specifically with objective components in the sample. In this case, it is also possible to develop the sample to react the reagents specifically with the objective components and then develop a detectable label substance which reacts with the resulting reaction products.

When the analytical process of this invention is employed, for example, three components in the same sample can be analyzed at the same time as described below.

First, in a development layer composed of a carrier in which a sample is to be developed, a sample, for example, a blood sample is subjected to electrophoretic migration by applying an electric field to the development layer, or moved by column chromatography, or moved on a thin layer. The blood sample thus moved arrives at a portion holding a first reagent which reacts specifically with an objective component in the sample. After the arrival, a reaction of only the corresponding item begins. An antigen or antibody in the blood sample reacts specifically with the first reagent. The residual components in the sample which do not react with the reagent continue to be moved and arrive at a place of the second reagent. A reaction of only the corresponding second item takes place therein.

The sample further continues to be moved and arrives at a portion holding a third reagent which reacts with a component in the sample different from the components reacted with the first and second reagents. After the arrival, an antigen or antibody reacts specifically with the reagent. After the residual biological components which do not react with the first, second and third reagents pass the third reagent place completely, the amounts of the three reaction products still held in the development layer are measured, for example, optically, and from these amounts, the concentration of components in the sample are calculated at the same time or successively.

The speed of movement of the sample in the development layer is adjusted so as to be sufficient for the reactions of the reagents with the objective components in the sample and permit holding of the reaction products in the development layer. According to such an immunoassay, in measuring the reaction products, contaminants in the sample are removed from the detection systems by moving the sample, so that analysis can be carried out without any influence of the contaminants. Therefore, analysis with high precision becomes possible.

When a chelating agent is used as a marker for detecting the reactions and chelate compounds are detected, whether any reaction product is present or not can be judged with naked eyes. Accordingly, the above-mentioned immunoassay is applicable also to analysis of many samples for the purpose of, for example, screening a plurality of components. When the reaction products are measured by using an optical or electric means, not only qualitative analysis but also quantitative analysis of components in a sample can be carried out. The optical measurement suitably comprises irradiation with monochromatic light, detection of the reflected light, calculation of the concentrations of test items from the intensity of the reflected light, and display thereof. In some cases, selection of said means for examination permits measurement even by detection of transmitted light.

As the electric means, in the case of, for example, an analytical process using a combination of electrophoresis and liposome, there can be exemplified a method which comprises placing in the liposome a substance detectable by means of electrodes, for example, $Na^+$ together with an antigen or the like, reacting an objective component with the liposome, then taking out a solution of the liposome, determining a substance which has flowed out of the liposome by use of a sensor of the electrode, and quantitating the objective component from the amount of signal in the electrode.

This invention is further explained below referring to Examples, which are not intended to limit the present invention but rather illustrate the present invention.

EXAMPLE 1

Figure 1:
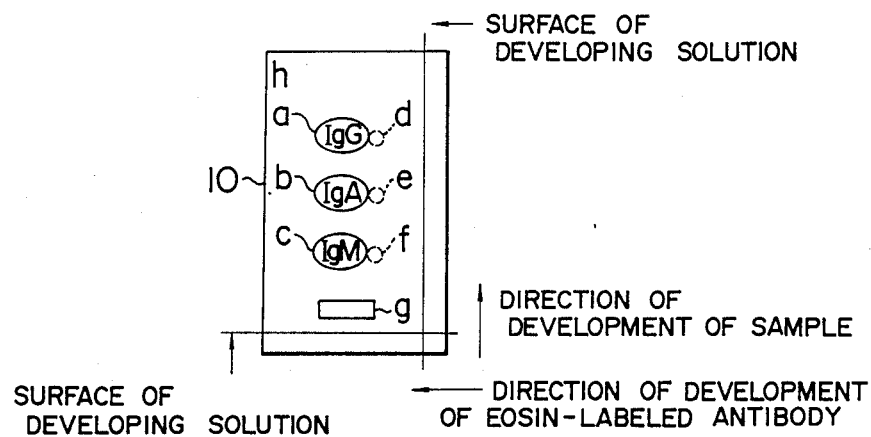
FIG. 1 is a scheme of a development layer material which is one embodiment of the means of this invention.

In FIG. 1 is shown an example of development layer used in qualitative analysis of IgG, IgA and IgM (immunoglobulins). As a carrier for a development layer, a cellulose gel (e.g., Sepharose-4B, a trademark, mfd. by Pharmacia Chemicals) was used. Binding of antibodies to Sepharose-4B was conducted in the following manner. Sepharose-4B activated with cyanogen bromide was sufficiently washed with a 0.2 M carbonate buffer (pH 8.8), after which an antibody was added in an amount of 10 mg (based on dry base) per ml of the Sepharose-4B activated with cyanogen bromide, and the resulting mixture was shaken overnight at 4° C. to bind the antigen to the Sepharose-4B.

Glycine was added in an amount of 0.2 g per ml of the above-mentioned reaction solution, and the resulting mixture was shaken at 4° C. for 8 hours to react glycine with -NH groups not bound to the antibody. In the manner described above, each of anti-IgG, anti-IgA and anti-IgM was bound to Sepharose-4B to prepare anti-IgG-Sepharose-4B, anti-IgA-Sepharose-4B and anti-IgM-Sepharose-4B.

The development layer was prepared in the following manner. Sepharose-4B suspended in a 0.1M phosphate buffer (pH 7.4) was formed into a smooth layer of 1 mm in thickness on a flat glass plate. In order to place the anti-IgG-, anti-IgA- or anti-IgM-bound Sepharose-4B's on the smooth layer, a thin layer was removed from the smooth layer in three places, and the antibody-bound Sepharose-4B's were placed at the places a, b and c in FIG. 1 so as to become smooth. At some distance from these places, a well g was formed as a sample-spotting place. The well g was formed so as to be somewhat concave and about 1 mm in the depth in order to facilitate spotting a sample.

The development layer material 10 in FIG. 1 has Sepharose-4B as a carrier. The place a has anti-IgG, the place b anti-IgA, and the place c canti-IgM.

EXAMPLE 2

Figure 3:
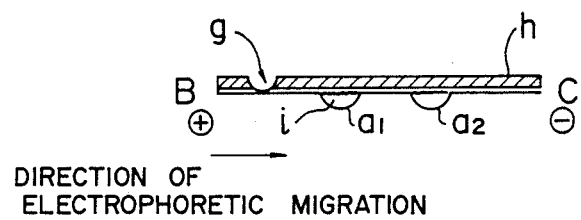
FIG. 3 is a side view of the means in FIG. 2.

This example relates to a kit for simultaneous quantitative analysis of three hormones in serum by use of the immunoassay according to this invention. Its development layer is shown in FIG. 2 and FIG. 3. As a carrier for the development layer, agarose gel was used. The sample-spotting place g was formed by removing a part of the agarose gel. Reagents reactive specifically to components in a sample in the development layer were located at the places $a_1$ and $a_2$, and they contained liposome. Preparation of a liposome membrane was conducted according to the method of C. T. Tain, Samuel W. Chan, et al. described in Methods in Enzymology 74, 152–161. Binding of each antibody to the liposome was conducted according to the method of Lee et al. described in Nature, 288, 602 (1985). A commercially available chelating agent TAMSMB was enclosed in the membrane according to a conventional method. A mesh i made of a porous material was provided between the gel and each reagent containing the liposome membrane to prevent movement of the liposome membrane and enable passage of components in the reagent.

Next, this invention is explained below referring to Experiment Examples of the analytical process of this invention.

EXPERIMENT EXAMPLE 1

In the sample-spotting place g of the kit according to Example 1 was spotted 5 μl of a sample containing IgG, IgA and IgM, and developed by using a 0.1M phosphate buffer as a developing solution. After the sample arrived at the top end of the development layer, eosin-labeled anti-IgG was spotted at the place d, eosin-labeled anti-IgA at the place e, and eosin-labeled anti-IgM at the place f. The eosin-labeled antibodies were developed in a direction perpendicular to the direction of development of the sample. As a developing solution, a 0.1M phosphate buffer (pH 7.4) was used. As a result, it was confirmed with the naked eye that IgG, IgA and IgM, i.e., components in the sample held in the development layer were labeled by eosin. The results obtained are shown in Table 1. The presence of IgG, IgA and IgM added to a sample was in substantial agreement with the color of eosin observed with the naked eye.

When urine was used as a sample, it was confirmed that three proteins could be qualitatively analyzed at the same time.

TABLE 1

Experiment Example 1. Result of Qualitative Analysis of IgG, IgA and IgM

| Sample No. | IgG (I) | IgG (II) | IgA (I) | IgA (II) | IgM (I) | IgM (II) |
|---|---|---|---|---|---|---|
| 1 | − | − | − | − | − | − |
| 2 | + | + | − | − | − | − |
| 3 | − | − | + | + | − | − |
| 4 | − | − | − | − | + | + |
| 5 | + | + | + | + | − | + |
| 6 | − | − | + | + | + | − |
| 7 | + | + | − | − | + | + |
| 8 | + | + | + | + | + | + |

(I) Added +, No addition −
(II) Results of measurement by the present process

EXPERIMENT EXAMPLE 2

Experiments were carried out by using the kit prepared in Example 2. A phosphate buffer (pH 6.0) was used as an electrophoresis buffer, and 5 μl of a sample spotted in the sample-spotting place g was subjected to electrophoretic migration by applying an electric current between B and C. Liposome having anti-thyroxine ($T_4$) bound thereto was contained in the place $a_1$ in the development layer 10 and liposome having anti-triiodothyronine ($T_3$) bound thereto was contained in the place $a_2$. When the sample passed the places $a_1$ and $a_2$, each component in the sample reacted specifically with each antibody on the liposome membrane contained on the other side of the mesh i shown in FIG. 3, whereby the objective components were held on the liposome membranes. The sample was subjected to electrophoretic migration from the anode B to the cathode C, after which 10 μl of a reagent prepared by adding a complement and a metal to phosphate buffer was injected into each of $a_1$ and $a_2$ to be reacted with the liposome membrane. The liposome membrane bound to an antigen in the sample was broken by the lytic activity of the complement, and the chelating agent TAMSMB enclosed in the liposome membranes flowed out. The chelating agent TAMSMB reacted with the metal to form a chelate and develop color. Twenty minutes after the injection of the complement and the metal, $T_3$ and $T_4$ in the sample were quantitated from absorbance at a wavelength of 585 nm.

Figure 4:
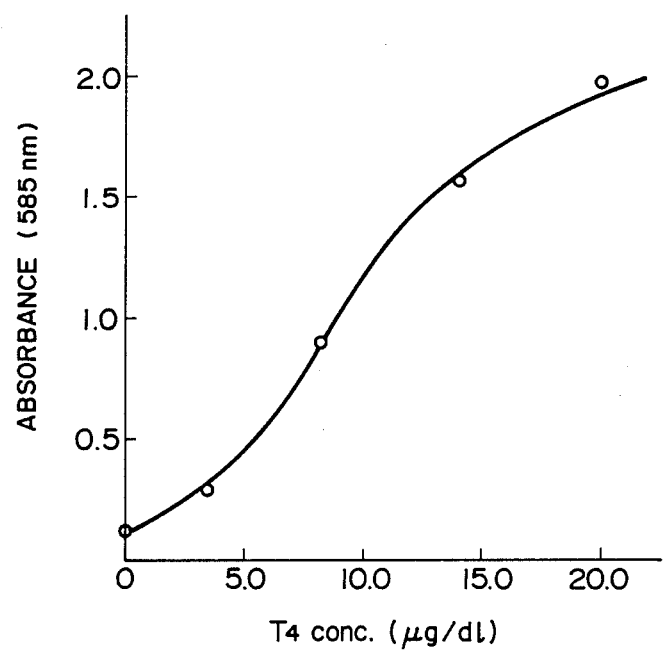
FIG. 4 is a graph showing an example of calibration curve of $T_4$.
Figure 5:
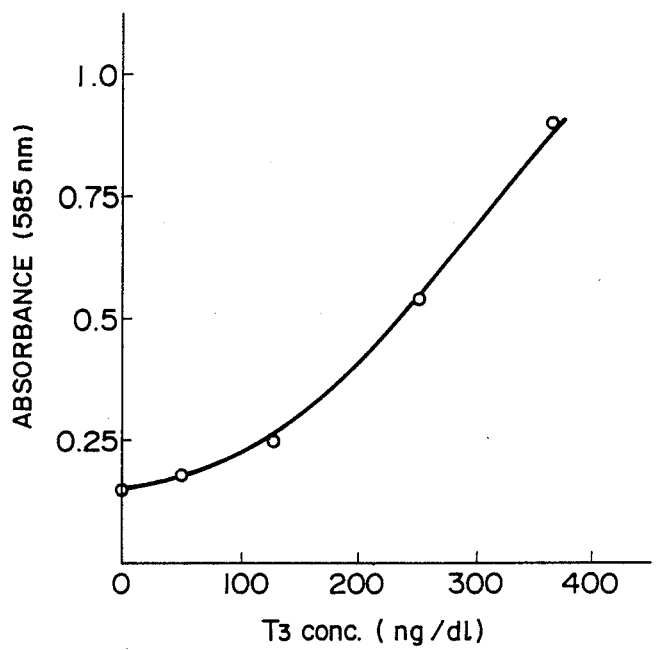
FIG. 5 is a graph showing an example of calibration curve of $T_3$.

The calibration curves in FIG. 4 and FIG. 5 were obtained by taking five concentrations of each of $T_3$ and $T_4$. From the calibration curves, $T_3$ and $T_4$ in the sample were determined. As a result of addition and recovery experiments, measured values in substantial agreement with the adding amounts were obtained. The results obtained are shown in Table 2. From the experiment results, it was confirmed that simultaneous determination of $T_1$ and $T_4$ in serum is possible.

TABLE 2

| | Component | | | | | |
|---|---|---|---|---|---|---|
| | Adding amount | | Measured value | | | |
| Sample No. | $T_3$ (ng/dl) | $T_4$ (μg/dl) | $T_3$ Abs | $T_3$ ng/dl | $T_4$ Abs | $T_4$ (μg/dl) |
| 1 | 46.5 | 2.5 | 0.175 | 50.2 | 0.225 | 2.2 |
| 2 | 172.6 | 6.8 | 0.368 | 181.4 | 0.550 | 5.9 |
| 3 | 269.7 | 13.6 | 0.619 | 275.7 | 1.625 | 14.5 |
| 4 | 141.7 | 5.6 | 0.298 | 148.9 | 0.488 | 5.3 |
| 5 | 0.0 | 0.0 | 0.150 | 4.8 | 0.135 | 0.5 |

EXPERIMENT EXAMPLE 3

α-Fetoprotein (α-FP) and C-reactive-protein (CRP) in a sample were quantitated by disc electrophoresis. Liposome was prepared in the same manner as in Example 2 mentioned above. Each of anti-α-FP and anti-CRP was bound to the surface of the liposome by a conventional method.

As a development layer, polyacrylamide gel was used. For preparing the gel, acrylamide and N,N'-methylbisacrylamide (Bis) were used as monomers, and N,N,N',N'-tetramethylethylenediamine (TEMED) and ammonium persulfate or riboflavin were used as polymerizing catalysts. A recipe for 7% gel (pH 9.5) is shown in the table 3.

TABLE 3

Process for Preparing Reagents for Producing a Gel for Disc Electrophoresis

| Solution | Composition | | |
|---|---|---|---|
| Solution A (pH 8.9) | 1N HCl | 24 ml | |
| | Tris | 18.1 g | |
| | TEMED | 0.12 ml | Made up with water to 50 ml |
| Solution B | 1N HCl | 48 ml | |
| | Tris | 5.98 g | |
| | TEMED | 0.46 ml | Made up with water to 100 ml |
| Solution C | Acrylamide | 28.0 g | |
| | Bis | 0.735 g | Made up with water to 50 ml |
| Solution D | Acrylamide | 20.0 g | |
| | Bis | 5.0 g | Made up with water to 100 ml |
| Solution E | Reboflavin | (4.0 mg) | was made up with water to 100 ml |
| Solution F | Sucrose | 40.0 g | Made up with water to 100 ml |
| Solution a for separating-gel | Solution A and Solution C were mixed in an equal amount | | |
| Solution b for | Ammonium persulfate (0.14 g) was made | | |

TABLE 3-continued

Process for Preparing Reagents for Producing a Gel for Disc Electrophoresis

| Solution | Composition |
|---|---|
| separating-gel | up with water to 100 ml |
| Solution for concentrating-gel | Solutions B, D, E and F and water were mixed in the ratio of 1:1:1:4:1. |
| Buffer for electrodes | Undiluted solution: Tris (6.0 g) and glycine (28.8 g) were made up with water to 1 liter (pH 8.3). The undiluted solution was used after being diluted 10-fold. |

A glass tube (inside diameter 8 mm, outside diameter 10 mm, and length 50 mm) was fixed vertically on a stand for preparing a gel. A solution for concentrating-gel was prepared by mixing in the manner shown in the table and solution a and solution b were prepared by mixing in the manner shown in the table immediately after deaeration. The solution for concentrating-gel was placed in the glass tube to the height of 10 mm from the bottom, and water was gently placed on the upper part of this solution. Gelation was conducted by carrying out photopolymerization by irradiation with light from a fluorescent lamp. The irradiation was carried out for about 20 minutes. Next, a solution for separating-gel was prepared by mixing in the manner shown in the table, and a solution of liposome having anti-α-FP bound thereto was deaerated and then mixed with an equal amount of the solution for separating-gel. The water covering the upper part of the gel in the glass tube was removed, and the solution for separating-gel containing the liposome was placed on the residue to a thickness of 5 mm. Water was gently placed on the upper part of this solution, and the glass tube was allowed to stand for about 30 minutes. Further, 15 mm of the same solution for concentrating-gel as described above was placed on the water, after which water was placed thereon, and the solution was subjected to photopolymerization. Then, a solution of liposome having anti-CRP bound thereto was mixed with an equal amount of a solution for separating-gel (a mixture of solution a and solution b). The resulting mixture was placed on the water in the glass tube and subjected to polymerization. The same solution for concentrating-gel as described above was placed on the resulting gel to a thickness of 10 mm and subjected to photopolymerization.

Figure 6:
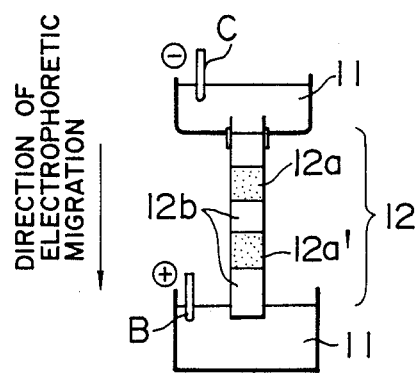
FIG. 6 is a scheme of a means used in Experiment Example 3.

A means was set up as shown in FIG. 6 by using the gel prepared in the manner described above. As a buffer for electrodes, the solution shown in the table 3 was used. To the sample was added an equal amount of a 20 % sucrose solution, and 5 μl of the resulting mixture was applied to the top end of the disc for electrophoresis. After electrophoresis was finished, the separating-gels containing each liposome were cut out and a complement solution was added, after which antigen-antibody reaction was measured. When carboxylfluorescein was previously enclosed in the liposomes, α-FP and CRP could be quantitated from the amount of fluorescence. When a chelating agent, for example, TAMSMB was enclosed in the liposomes, they could be quantitated from light absorption when copper ion $Cu^{2+}$ was added in addition to the complement.

Figure 7:
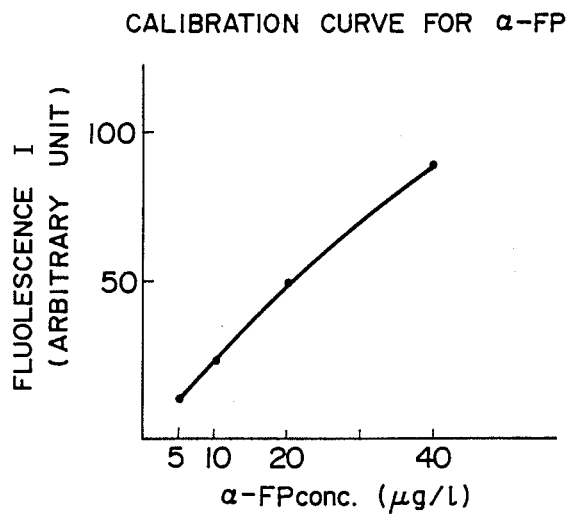
FIG. 7 is a graph showing an example of calibration curve of α-FP.
Figure 8:
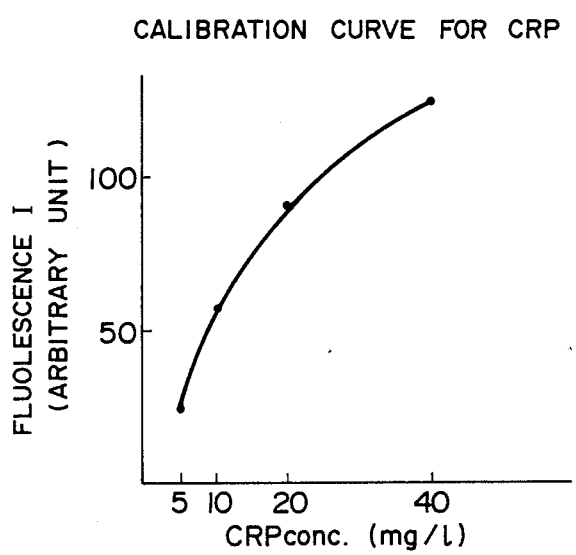
FIG. 8 is a graph showing an example of calibration curve of CRP.

There were used samples having α-FP concentration of 5 μg/liter, 10 μg/liter, 20 μg/liter or 40 μg/liter, and samples having CRP concentration of 5 mg/liter, 10 mg/liter, 20 mg/liter or 40 mg/liter, and each of the samples was subjected to electrophoresis, after which separating-gel was cut out, and calibration curves were obtained from the amount of fluorescence (carboxyfluorescein). They are shown in FIGS. 7 and 8.

According to the present invention, as is clear from the above Examples, there can be provided an immunoassay for qualitatively or quantitatively analyzing various biological components at the same time by using a slight amount of a single test sample obtained by sampling and a kit used therefor. In particular, this immunoassay is advantageous in that no contaiminant is present at the time of analysis because objective components can be separated from other components in the development layer by using the present kit. Further, simultaneous analysis of a plurality of objective components is made possible by changing the kind and number of reagents supported on the development layer.

What is claimed is:

1. A kit for simultaneous immunoassay of at least two items in a single sample, which comprises:
    a single development layer;
    a concave-sample spotting well formed within said layer and located adjacent to one end of the development layer, said development layer comprising a development layer material permitting immobilization of reagents and permitting development of the single sample containing at least two items by movement of the sample by diffusion or by electrophoresis from the well towards another end of the development layer;
    at least two reagents for testing said at least two items in said sample, each of said at least two reagents being enclosed in microcapsules and immobilized at two different locations spaced apart from each other and at appropriate positions along a path of movement of the sample within isolated portions of the development layer, each location containing a different antigen or antibody; and
    a detectable label substance enclosed in said microcapsules with said antigen or antibody.

2. An immunoassay kit according to claim 1, wherein the development layer is made of a material selected from the group consisting of synthetic polymers, polysaccharides, proteins, metal hydroxides, zeolites, porous glass beads and porous plastic films.

3. An immunoassay kit to claim 1, wherein each microcapsule is composed of a liposome membrane.

4. An immunoassay kit according to claim 1, wherein said locations immobilizing said at least two reagents are separate and distinct portions where a thin layer of said development layer has been removed;
    and wherein said antibody or antigen contained at each of said locations is developed in a direction perpendicular to a direction of development of a sample spotted at said sample-spotting well, said sample diffusing across said locations.

5. An immunoassay kit according to claim 4, wherein said sample-spotting well is provided in the same place as one of said reagent-containing locations.

6. An immunoassay kit according to claim 4, wherein said sample-spotting well is provided remotely from said reagent-containing locations.

7. An immunoassay kit according to claim 1, wherein said at least two reagents each comprise a lipsome solution having an antibody or antigen bound thereto;

and wherein said locations for immobilizing said at least two reagents are covered with a porous mesh.

8. An immunoassay kit according to claim 1, wherein said kit further includes means for applying an electric current to cause a sample spotted at said sample-spotting well to migrate from said well to each of said locations.

9. An immunoassay kit according to claim 1, wherein said label substance is selected from the group consisting of chelating agents, enzymes, coenzymes and fluorescent substances.

10. An immunoassay kit according to claim 1, wherein said development layer is formed on a glass substrate.